(12) United States Patent
Schmidt

(10) Patent No.: US 11,062,441 B2
(45) Date of Patent: Jul. 13, 2021

(54) METHOD AND COMPUTER SYSTEM FOR ANALYZING IMAGE DATA OF A PATIENT

(71) Applicant: Siemens Healthcare GmbH, Erlangen (DE)

(72) Inventor: Sebastian Schmidt, Weisendorf (DE)

(73) Assignee: Siemens Healthcare GmbH, Erlangen (DE)

( * ) Notice: Subject to any disclaimer, the term of this patent is extended or adjusted under 35 U.S.C. 154(b) by 107 days.

(21) Appl. No.: 15/987,108

(22) Filed: May 23, 2018

(65) Prior Publication Data
US 2018/0342057 A1    Nov. 29, 2018

(30) Foreign Application Priority Data
May 23, 2017    (EP) .................................. 17172462

(51) Int. Cl.
    *G06K 9/00*        (2006.01)
    *G06T 7/00*         (2017.01)
    *G06F 16/583*     (2019.01)
    *G16H 50/20*      (2018.01)
    *G06F 9/455*      (2018.01)
    *G16H 10/60*      (2018.01)
    *G16H 40/40*      (2018.01)

(52) U.S. Cl.
CPC ........ *G06T 7/0012* (2013.01); *G06F 9/45558* (2013.01); *G06F 16/5838* (2019.01); *G16H 50/20* (2018.01); *G06F 2009/4557* (2013.01); *G16H 10/60* (2018.01); *G16H 40/40* (2018.01)

(58) Field of Classification Search
CPC .................................................. G06T 7/0012
See application file for complete search history.

(56) References Cited

U.S. PATENT DOCUMENTS 9,384,413 B2    7/2016   John et al.
2006/0098855 A1   5/2006   Gkanatsios et al.
(Continued)

OTHER PUBLICATIONS

European Examination dated Oct. 18, 2019, for Application No. 17 172 462.8.
(Continued)

*Primary Examiner* — Oneal R Mistry
(74) *Attorney, Agent, or Firm* — Schiff Hardin LLP

(57) ABSTRACT

A first image data set of a patient is provided to a computer, and the computer performs a first analysis of the first image data set using a first analysis algorithm that is designed for an analysis purpose. After completion of the first analysis, a second analysis algorithm is added to a database to which the computer has access, so that the second analysis algorithm is now available for access by the computer. The second analysis algorithm is designed for the same purpose as the first analysis algorithm. After the second analysis algorithm has been added to the database, a second image dataset of the patient is provided to the computer. Even though the second analysis algorithm is now available to the computer for the same analysis purpose as the first analysis algorithm, the computer automatically defaults to use the first analysis algorithm to perform a second analysis of the second image data set. This helps to ensure that the first analysis and the second analysis are comparable to each other, because they have been performed by the same analysis algorithm.

19 Claims, 1 Drawing Sheet

(56) References Cited

U.S. PATENT DOCUMENTS

| | | | |
|---|---|---|---|
| 2014/0200433 A1* | 7/2014 | Choi | A61B 5/4887 |
| | | | 600/407 |
| 2016/0035074 A1* | 2/2016 | Jeong | G06T 3/40 |
| | | | 382/282 |
| 2016/0048965 A1* | 2/2016 | Stehle | G06T 7/0016 |
| | | | 382/131 |
| 2016/0093045 A1 | 3/2016 | Koyasu et al. | |
| 2016/0171157 A1* | 6/2016 | Mielekamp | G06T 11/60 |
| | | | 345/589 |
| 2016/0180052 A1 | 6/2016 | Godenschwager et al. | |
| 2016/0210745 A1* | 7/2016 | Yoshida | G06F 19/321 |
| 2017/0061654 A1* | 3/2017 | Litvin | A61B 6/482 |
| 2017/0086797 A1* | 3/2017 | Halmann | G06F 21/6245 |
| 2017/0119334 A1* | 5/2017 | Smith | G06T 7/0016 |
| 2018/0075628 A1* | 3/2018 | Teare | A61B 6/461 |
| 2018/0329609 A1* | 11/2018 | De Swarte | G06T 19/00 |
| 2019/0239843 A1* | 8/2019 | Bregman-Amitai | A61B 6/032 |

OTHER PUBLICATIONS

"Runtime System," Wikipedia article (2016).
"Runtime Environment (RTE)," Techopedia article (2016).
"Virtual Machine," Wikipedia article (2016).
"Laufzeitumgebung," German Wikipedia article (2016).

\* cited by examiner

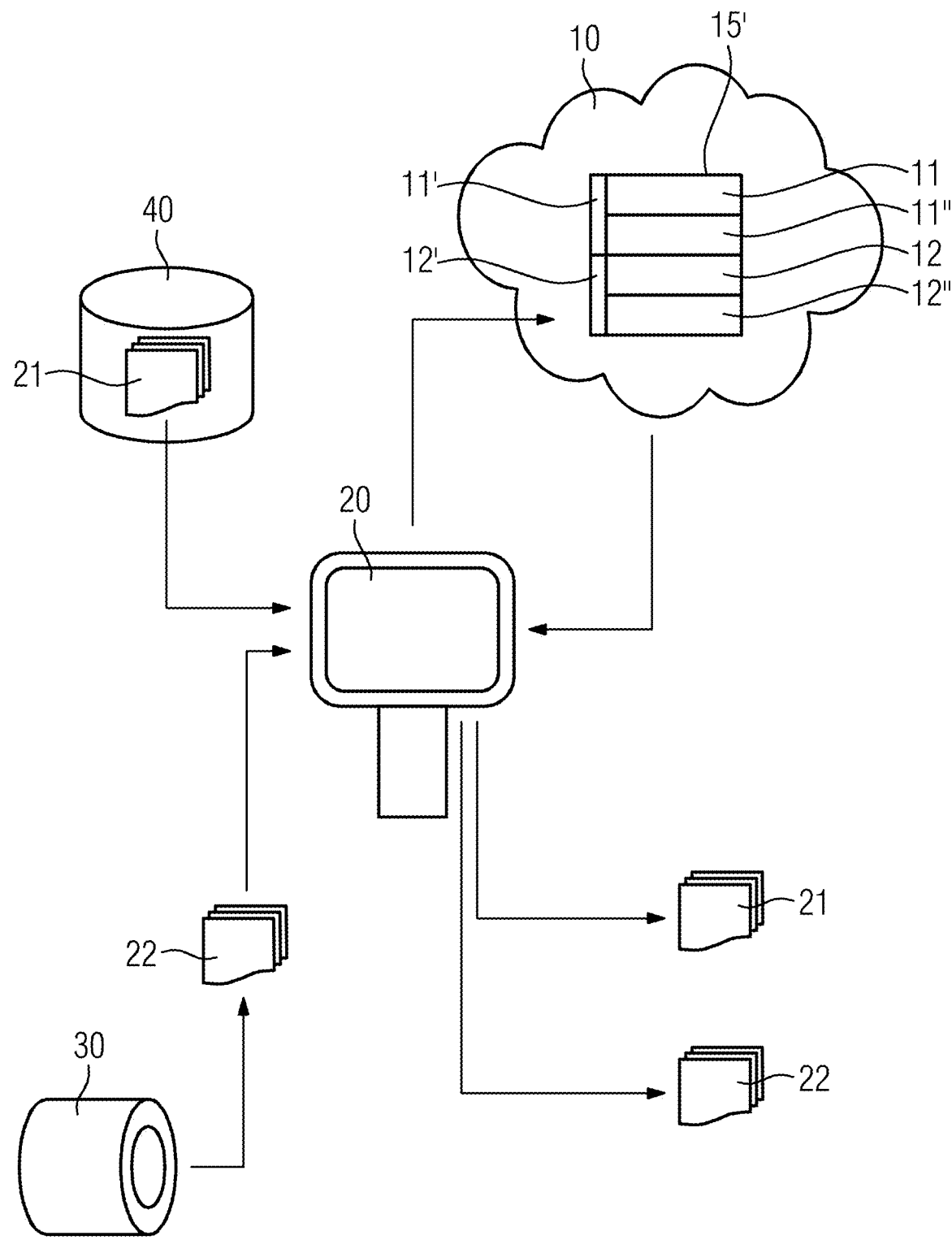

METHOD AND COMPUTER SYSTEM FOR ANALYZING IMAGE DATA OF A PATIENT

BACKGROUND OF THE INVENTION

Field of the Invention

The present invention concerns a method for analyzing image data of a patient, a computer system for performing such a method for analyzing image data of a patient, and a non-transitory, computer-readable data storage medium encoded with programming instructions (code) for implementing such a method.

Description of the Prior Art

Analyzing image data of a patient, in particular analyzing image data automatically, is well known. Typically, an analysis algorithm recognizes and/or measures a pathology that is visible in the image data of the patient. For example, a CT-image is recorded by a corresponding imaging scanner and the analysis of the recorded CT-Image is performed by the analysis algorithm, wherein the analysis algorithm emits, an output, a numerical value of the size of the pathology, such as a pulmonary node. For observing the potential growth of the pathology, the patient might revisit the hospital several times over a long time span, a new image data set is recorded and analyzed at each visit.

However, the analysis algorithm and/or operation system of workstations being used for running the analysis algorithm changes over time. Therefore, the same analysis algorithm may not be used for several different image data sets of the same patient that are obtained at different times.

Methods for the analysis of image data are known for example from US 2016/0180052 A1 and U.S. Pat. No. 9,384,413 B2.

SUMMARY OF THE INVENTION

An object of the present invention is to provide a method for analyzing several image data sets of a patient, wherein the method yields outputs over time that are comparable.

In accordance with the invention, a first image data set of a patient is provided to a computer, and the computer performs a first analysis of the first image data set using a first analysis algorithm that is designed for an analysis purpose. After completion of the first analysis, a second analysis algorithm is added to a database to which the computer has access, so that the second analysis algorithm is now available for access by the computer. The second analysis algorithm is designed for the same purpose as the first analysis algorithm. After the second analysis algorithm has been added to the database, a second image dataset of the patient is provided to the computer. Even though the second analysis algorithm is now available to the computer for the same analysis purpose as the first analysis algorithm, the computer automatically defaults to use the first analysis algorithm to perform a second analysis of the second image data set. This helps to ensure that the first analysis and the second analysis are comparable to each other, because they have been performed by the same analysis algorithm.

Contrary to the state of the art, according to the present invention the first analysis algorithm is used for both the first image data set and the second image data set, even though the second analysis algorithm is available at the time of providing the second image data set. The first analysis algorithm and the second analysis algorithm are both intended for postprocessing the first and second image data set for the same purpose, for example for measuring a volume of a lesion. The first analysis algorithm and the second analysis algorithm can be a band filter, a reconstruction from row data, a quantitative evaluation or a similar process. Providing the first and the second image data set includes recording an image by operation of an imaging modality, such as a CT-, NMR-, PET- or X-Ray-scanner. The server can be separated in space from a workstation at which the first and the second analysis algorithms are executed. Preferably, the server is configured as cloud and/or as part of a network and/or is incorporated into the workstation. Furthermore, there is a processor included in the server and/or workstation for executing the first and/or second analysis algorithms. Adding the second analysis algorithm occurs after analyzing the first image data set using the first analysis algorithm. Furthermore, the first analysis algorithm concerns the same output as the second analysis algorithm. For example, both the first and the second analysis algorithms can provide the volume of a lesion as an output. Preferably, the second analysis algorithm is an improved version of the first analysis algorithm, i.e. an upgraded or updated version of the first analysis algorithm. The second image data set is analyzed by the first analysis algorithm, even though the second analysis algorithm is available and is an improved version of the first analysis algorithm. For example, the second analysis algorithm can be an improved method for correcting a partial volume compared to the first analysis algorithm. By adding the second analysis algorithm to the database, it is still possible to access the second analysis algorithm and make use of its benefits when appropriate. The user thus does not have to forego the advantages that the second analysis algorithm can provide outside of the situation where output compatibility with the previously-used first analysis algorithm is desired.

Preferably, a first container for the first analysis algorithm and a first run time environment is stored in the database and/or a second container for the second analysis algorithm and a second run time environment is stored in the database. The first and/or second containers respectively wrap software in a complete filesystem that contains everything the first analysis algorithm or second analysis algorithm needs to run: code, run time, system tools, system libraries—anything that can be installed on the workstation. This ensures that the first analysis algorithm and/or the second analysis algorithm will always run the same way, regardless of the environment it is running in. Thus, it is possible to run the first analysis algorithm and/or the second analysis algorithm at the workstation independently form the operation system used by the workstation. Consequently, the first analysis algorithm can be executed by the workstation, even in the case of operation system of the workstation having changed in the meantime. Thereby, the use of containers or a container structure simplifies transferring and installing of the first analysis algorithm. Another advantage of using a container, in particular a closed container, is that there is no need for starting another operation system at the workstation.

According to another aspect of the present invention, a first virtual machine is stored in the database along with the first analysis algorithm and/or a second virtual machine is stored along with the second analysis algorithm in the database. A virtual machine (VM) is an emulation of an operation system. Virtual machines are based on computer architectures and provide the functionality of a physical computer. By providing the virtual machine it is possible to execute the first analysis algorithm on the workstation, even if the operation system on the workstation has changed.

The first image data set and/or the second image data set is marked for assigning the first image data set and/or second image data set to the patient. Thus, it is possible to assign the respective first analysis algorithm to the patient and select the proper first analysis algorithm for analyzing the second image data set. For example, the first image data set is saved to a memory, in particular to a picture archiving and communication system (PACS), along with an item of information about the first analysis. The item of information might be the version of the analysis algorithm. Further, the memory can be separated from the workstation in space. Preferably, the item of information about the first analysis algorithm is incorporated into the digital imaging and communications in medicine (DICOM) header that is used as a standard for handling, storing, printing, and transmitting items of information in medical imaging. It is also possible to incorporate the item of information about the first analysis algorithm into an RIS (Radiology information system), an HIS (hospital information system) or other IT-systems. By marking the first image data set and/or second image data set it is possible to identify the first analysis algorithm that was used in the past for performing the analysis of the first image data set.

In an embodiment of the present invention, the first analysis algorithm, the first container and/or the first virtual machine is automatically selected from the database for performing the analysis of the second image data set. Thus, there is no further activity of the user needed for selecting the first analysis algorithm. For example, the workstation identifies the first analyzing algorithm corresponding to the patient and selects the first analysis algorithm, the first container and/or the first virtual machine for analyzing the second image data set. The output of the analysis by the first analysis algorithm can be compared to the output of the analysis by the second analysis algorithm and any difference between the outputs is identified, in particular displayed on a screen of the workstation, automatically. Thus, the user is immediately informed about a change of the outputs or the observed pathology.

According to a preferred embodiment it is provided that the first container, the first virtual machine and/or first analysis algorithm is transferred from the database to a workstation. Thus, the first analysis algorithm can be executed on the work-station. Preferably, the workstation has a processor being configured for accessing to the server, in particular to the database, and for executing the first analysis algorithm, the second analysis algorithm, the first virtual machine, the second virtual machine, the first run time environment and/or the second run time environment. It is also conceivable that only the first analysis algorithm is electively transferred to the workstation in the case that the operation system or the version of the operation system has not changed since performing the analysis of the first image data set. Thus, a relatively small amount of data need to be transferred. It is also conceivable that the workstation performing the analysis of the first image data set and the workstation performing the analysis of the second image data set differ.

In another embodiment, the server is shared by several workstations. Thus, several workstations can use the same server. That means it is not necessary to realize and update a database for each workstation. Furthermore, several workstations share one common memory for saving the first image data set along with the item of information about the first analysis algorithm. In particular, "sharing" means in this context that several workstations have access to one common server and/or one common memory device. Preferably, the one common server is separated from the common memory device in space. It is also possible for several hospitals to share a common server, whereas each hospital has access only to its own memory for saving the first image data set along with the item of information about the first analysis algorithm.

By making an appropriate input into the workstation computer, the user can still make use of both the first analysis algorithm and the second analysis algorithm in order to perform an analysis of the second image data set. Thus, the user can use the first analysis algorithm for getting comparable results to the analysis of the first image data set and can use the second analysis algorithm for getting a more detailed or improved analysis. For example, the user can override the automatic default to use the first analysis algorithm so as to choose between applying the first analysis algorithm and the second analysis algorithm. It is also conceivable for the method to provide outputs that result both from the first analysis algorithm and the second analysis algorithm.

The present invention also encompasses a system having a computer and a database wherein the computer is configured to perform any or all of the embodiments of the method according to the invention, as described above.

According to a preferred embodiment of the present invention, it is provided that the system has a workstation at which the computer is present and/or an imaging scanner.

The present invention also encompasses a non-transitory, computer-readable data storage medium encoded with programming instructions that, when the storage medium is loaded into a computer that has access to a database, cause the computer to perform any or all of the embodiments of the method according to the invention, as described above.

BRIEF DESCRIPTION OF THE DRAWINGS

FIG. 1 schematically illustrates a preferred embodiment of the method according to the invention for analyzing image data of a patient.

DESCRIPTION OF THE PREFERRED EMBODIMENTS

In the FIG. 1, a method for analyzing image data of a patient according to a preferred embodiment is schematically illustrated. Such methods are intended for automatically interpreting and/or categorizing the content of an image data set, such as an X-ray image, a PET-scan image, and/or a NMR-scan image. For example, the method for analyzing image data measures the size and/or localizes a malformation being visible in the image data set of the patient. In a first step of the illustrated method a first image data set 21 of the patient is provided by an imaging scanner 30, such as a CT-, NMR-, PET- or X-ray-scanner. Subsequently, the first image data set 21 is analyzed by using a first analysis algorithm 11 at a workstation 20 having a processor for running the first analysis algorithm 11 in a second step. Thus, the attending doctor or user gets an output based on the first analysis algorithm. For example, the first analysis algorithm 11 automatically shows that a pulmonary node has a volume of 3, 4 $cm^3$. Afterwards the first image data set 21 is saved in a memory 40, preferably in a picture archiving and communication System (PACS), in a third step. An item of information about the first analysis algorithm 11 is saved along with the first image data set 21. Preferably, the item of information about the first analysis algorithm 11 is incorporated into the Digital Imaging and Communications in Medicine (DICOM) header that is used as a standard for handling, storing, printing, and transmitting items of information in medical imaging. It is also possible to incorporate the item of information about the first analysis algorithm 11 into an RIS (Radiology information system), an HIS (hospital information system) or other IT-systems. Due to the development of the operation systems used by the workstation 20 or due to upgrades of the analysis algorithm it cannot guaranteed that analyzing a second image data set 22 by using a second analysis algorithm 12 leads to the same result as analyzing a second image data set 22 by using the first analysis algorithm 11, wherein a time lag is between recording and/or analyzing the first image data set 21 on one hand and recording and/or analyzing a second image data set 22 on the other hand. Consequently, the output of the first analysis algorithm 11 cannot compared to the output of the second analysis algorithm 12. For guaranteeing that the outputs of the first analysis algorithm 11 and the second analysis algorithm 12 are comparable a server 10 having a database 15 for analysis algorithms is provided. For example, the server 10 is configured as cloud. In particular, the first analysis algorithm 11 and the second analysis algorithm 12 are stored on the database. Preferably, the first analysis algorithm 11 is available on the server 10 during the first and the second step, while the second analysis algorithm 12 is not available during the first and the second step and is added in a fourth step to the database 15 after the second step and/or the third step. Thus, it is possible to use the first analysis algorithm 11 for analyzing the second image data set 22. Preferably, the first analysis algorithm 11 is stored in a closed first container 11' that includes a first run time environment 11" and/or the second analysis algorithm 12 is stored in a second container 12' that includes a second run time environment 12". As a consequence, the first analysis algorithm 11 can advantageously run on a workstation 20 that might no longer compatible with the first analysis algorithm 11. For performing the analysis of the second image data set 22 it is provided that the second image date 22 set is assigned to the patient in a fifth step. Based on the item of information saved along with the first image data set 21 it is advantageously possible to select the first analysis algorithm 11 or the first container 11' from the database 15 for analyzing the second image data set 22. Preferably, the first analysis algorithm 11 or the first container 11' is transferred from the sever 10 to the workstation 20 or the workstation 20 runs the first analysis algorithm 11 by accessing the sever in a sixth step. Thus, both the first image data set 21 and the second image data set 22 can be analyzed by the same first analysis algorithm 11. For example, the first analysis algorithm 11 applied to the second image data set 22 shows that the size of the pulmonary nodules recognized in the first image data 21 set remains the same and the attending doctor comes to the conclusion that there is no cancer.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for analyzing image data of a patient comprising:
    providing a first image data set of a patient to a computer;
    from said computer, accessing a database in which a first analysis algorithm is stored in order to retrieve said first analysis algorithm, and using said first analysis algorithm to perform a first analysis of said first image data set for an analysis purpose for which said first analysis algorithm is designed;
    after performing said first analysis of said first image data set, adding a second analysis algorithm to said database that has the same analysis purpose as said first analysis algorithm, the second analysis algorithm being an updated version of the first analysis algorithm;
    after adding said second analysis algorithm to said database, providing a second image data set of the patient to the computer;
    from said computer, automatically defaulting to retrieve said first analysis algorithm from the database, rather than said second analysis algorithm, and using said first analysis algorithm to perform a second analysis of said second image data set so that both the first analysis and the second analysis are performed by said first analysis algorithm, thereby making said first analysis and said second analysis comparable to each other; and
    making a result of said first analysis and a result of said second analysis available as an output from said computer in electronic form.

2. A method as claimed in claim 1 comprising at least one of:
    storing said first analysis algorithm in said database together with a first run time environment in a first container; and
    storing said second analysis algorithm in said database together with a second run time environment in a second container.

3. A method as claimed in claim 1 comprising at least one of:
    storing a first virtual machine together with said first analysis algorithm in said database; and
    storing a second virtual machine together with said second analysis algorithm in said database.

4. A method as claimed in claim 1 comprising:
    marking each of said first and second image data sets with an identifier that identifies the respective first and second image data sets as being of said patient; and
    identifying the respective marker in said first image data set and in said second image data set in order to assign said first image data set to said patient and to assign said second image data set to said patient.

5. A method as claimed in claim 1 comprising storing said first analysis algorithm together with a first virtual machine in a first container of said database, and transferring at least one of said first container or said first virtual machine or said first analysis algorithm from said database to a workstation at which said computer is located.

6. A method as claimed in claim 5 comprising sharing said computer among a plurality of separate workstations.

7. A method as claimed in claim 1 comprising receiving a user input into said computer that causes said computer to also analyze said second image data set using said second analysis algorithm.

8. A method as claimed in claim 1 wherein, as the updated version of the first analysis algorithm, the second analysis algorithm is an improved version of the first analysis algorithm.

9. A method as claimed in claim 1 wherein the first analysis algorithm and the second analysis algorithm are configured for partial volume correction.

10. A method as claimed in claim 1 wherein the first analysis algorithm and the second analysis algorithm are configured for image data processing.

11. A method as claimed in claim 1 wherein:
performing the first analysis of the first image data set generates a first analysis output including a first value of a characteristic of a pathology of the patient; and
performing the second analysis of the second image data set generates a second analysis output including a second value of the same characteristic of the pathology of the patient.

12. A method as claimed in claim 11 wherein the characteristic of the pathology of the patient is a volume or size of the pathology.

13. A method as claimed in claim 1 wherein the analysis purpose of the first and the second analysis algorithms is to analyze a pathology of the patient and generate a corresponding analysis output including a respective value of a characteristic of the pathology.

14. A method as claimed in claim 13 wherein the characteristic of the pathology of the patient is a volume or size value of the pathology.

15. A method as claimed in claim 1 wherein the first analysis algorithm and the second analysis algorithm concern a same output characteristic.

16. A method as claimed in claim 1 wherein the second analysis algorithm has a same analysis output goal as the first analysis algorithm.

17. A method as claimed in claim 1 wherein the first analysis algorithm and the second analysis algorithm are configured to perform a same pathological analysis.

18. A system for analyzing image data of patient, said system comprising:
a computer provided with a first image data set of a patient; and
a database accessible by said computer, wherein:
said computer is configured to access said database in which a first analysis algorithm is stored in order to retrieve said first analysis algorithm, and to use said first analysis algorithm to perform a first analysis of said first image data set for an analysis purpose for which said first analysis algorithm is designed;
said database, after said first analysis of said first image data set is performed, has a second analysis algorithm added to said database that has the same analysis purpose as said first analysis algorithm, the second analysis algorithm being an updated version of the first analysis algorithm;
said computer, after adding said second analysis algorithm to said database, is provided with a second image data set of the patient;
said computer is configured to automatically default to retrieve said first analysis algorithm from the database, rather than said second analysis algorithm, and to use said first analysis algorithm to perform a second analysis of said second image data set so that both the first analysis and the second analysis are performed by said first analysis algorithm, thereby making said first analysis and said second analysis comparable to each other; and
said computer is configured to make a result of said first analysis and a result of said second analysis available as an output from said computer in electronic form.

19. A non-transitory, computer-readable data storage medium encoded with programming instructions, said storage medium being loaded into a computer having access to a database, and said programming instructions causing said computer to:
receive a first image data set of a patient;
access said database in which a first analysis algorithm is stored in order to retrieve said first analysis algorithm, and use said first analysis algorithm to perform a first analysis of said first image data set for an analysis purpose for which said first analysis algorithm is designed;
after said first analysis of said first image data set is performed, said database having a second analysis algorithm added to said database that has the same analysis purpose as said first analysis algorithm, the second analysis algorithm being an updated version of the first analysis algorithm;
after said second analysis algorithm was added to said database, receive a second image data set of the patient to the computer;
automatically default to retrieve said first analysis algorithm from the database, rather than said second analysis algorithm, and to use said first analysis algorithm to perform a second analysis of said second image data set so that both the first analysis and the second analysis are performed by said first analysis algorithm, thereby making said first analysis and said second analysis comparable to each other; and
make a result of said first analysis and a result of said second analysis available as an output from said computer in electronic form.

* * * * *